United States Patent [19]

Greenwell et al.

[11] Patent Number: 5,074,847
[45] Date of Patent: Dec. 24, 1991

[54] NEEDLE SHIELD WITH TRANSPARENCY MAINTAINING COATING

[75] Inventors: Charles H. Greenwell, El Dorado; Don W. Casey, deceased, late of Great Bend, by Katherine Ann Casey, legal representative; Gerald E. Wagnon, Great Bend, all of Kans.; James A. Miller, Silver Lake; Robert M. Shaw, Jr., Cuyahoga Falls, both of Ohio

[73] Assignee: Century Plastics, Inc., El Dorado, Kans.

[21] Appl. No.: 505,979

[22] Filed: Apr. 5, 1990

Related U.S. Application Data

[63] Continuation-in-part of Ser. No. 345,286, May 1, 1989, abandoned.

[51] Int. Cl.$^5$ .............................................. A61M 5/32
[52] U.S. Cl. ..................................... 604/174; 604/180; 128/888; 128/DIG. 26
[58] Field of Search ................ 604/122, 126, 174, 180, 604/45, 324, 333; 128/877, 887, 888, DIG. 6, DIG. 26; 106/13

[56] References Cited

U.S. PATENT DOCUMENTS

| | | | |
|---|---|---|---|
| 2,314,724 | 3/1943 | Marsan | 128/283 |
| 3,194,235 | 7/1965 | Cooke | 128/132 |
| 3,461,869 | 4/1966 | Hargest | 128/214 |
| 3,528,416 | 10/1970 | Chamberlain | 128/888 |
| 3,782,377 | 1/1974 | Rychlik | 128/132 |
| 3,782,378 | 1/1974 | Page | 128/133 |
| 3,856,534 | 12/1974 | Fletcher et al. | 106/13 |
| 3,900,026 | 8/1975 | Wagner | 128/133 |

(List continued on next page.)

FOREIGN PATENT DOCUMENTS

| | | | |
|---|---|---|---|
| 831757 | 7/1949 | Fed. Rep. of Germany | 30/303 |
| 2128481A | 5/1984 | United Kingdom . | |

OTHER PUBLICATIONS

Tyvek ® Spunbonded Olefin published by DuPont in Dec. 1978.
Chapter 21 Polyvinylpyrrolidone to Bleacher et al. (GAF Corp.) published before 4/4/89.
Pyrrolidone Based Polymers published before 4/4/89.
National Safety data sheet on Triton ® X-100 Surfactant issued on 3/30/89 by Rohm and Haas Co.

Primary Examiner—John D. Yasko
Assistant Examiner—Anthony Gutowski
Attorney, Agent, or Firm—John Wade Carpenter

[57] ABSTRACT

A device for holding a heparin lock secured to a catheter that has been previously disposed through a body portion and into an artery of a patient. The device has a cover having a wall constructed of generally flexible material. The wall includes a face having a continuous periphery and an aperture off-set from the continuous periphery. The wall additionally has a generally oval-shaped body integrally secured to the face along a substantial portion of the continuous periphery. The face and the oval-shaped body may include flanges secured at a lowermost portion thereof. The inside surface of the wall may be coated with a composition of matter that maintains the transparency of a transparent wall. The wall may also include one or more openings that are covered with one or more air permeable sheet members which are impenetrable by a liquid but allow vapor and moisture to pass through from the insides of the oval-shaped body when in a covering relation to a catheter in a body portion of a patient. A method for holding a heparin lock secured to a catheter that has been previously disposed through a body portion and into an artery of a patient. The method includes forming a hollow generally elongated cover having a face with an aperture, inserting a heparin lock into the aperture to substantially seal off the aperture, and securing the cover to the body portion to totally enclose the catheter while the heparin lock remains slidably lodged within the aperture.

16 Claims, 6 Drawing Sheets

U.S. PATENT DOCUMENTS

| | | | |
|---|---|---|---|
| 3,901,226 | 8/1975 | Scardenzan | 128/133 |
| 3,933,407 | 1/1976 | Tu et al. | 350/61 |
| 4,080,476 | 3/1978 | Laskey | 433/30 |
| 4,399,816 | 8/1983 | Spangler | 128/154 |
| 4,467,073 | 8/1984 | Creasey | 525/127 |
| 4,470,410 | 9/1984 | Elliott | 128/133 |
| 4,517,971 | 5/1985 | Sorbonne | 604/174 |
| 4,626,246 | 12/1986 | Verkade | 604/174 |
| 4,633,863 | 1/1987 | Filips | 128/165 |
| 4,679,553 | 6/1987 | Proulix et al. | 128/133 |
| 4,702,736 | 10/1987 | Kalt et al. | 604/180 |
| 4,743,232 | 5/1988 | Kruger | 604/180 |
| 4,781,695 | 11/1988 | Dalton | 604/175 |
| 4,808,162 | 2/1989 | Oliver | 604/180 |
| 4,846,807 | 7/1989 | Safadago | 604/179 |
| 4,898,587 | 2/1990 | Mera | 604/180 |

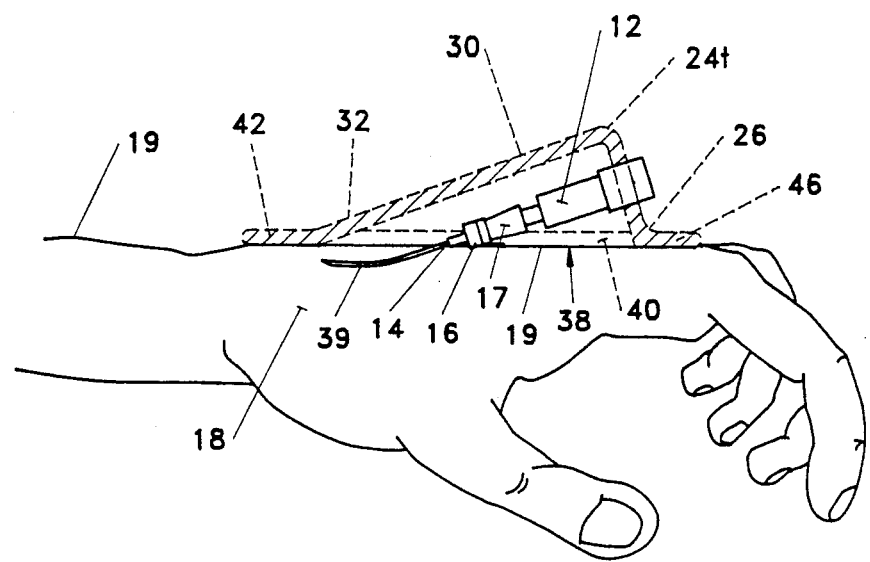
Fig. 12
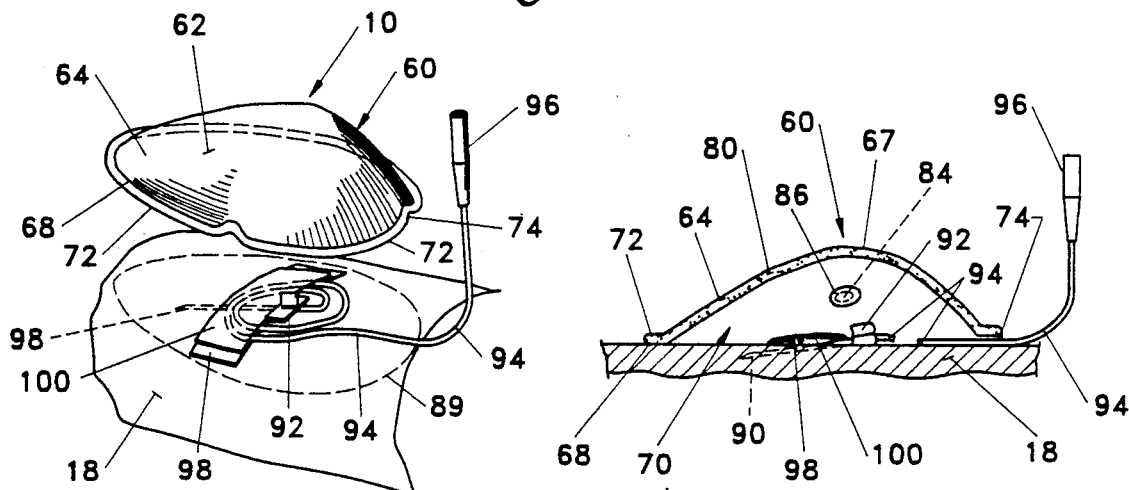
Fig. 13
Fig. 15
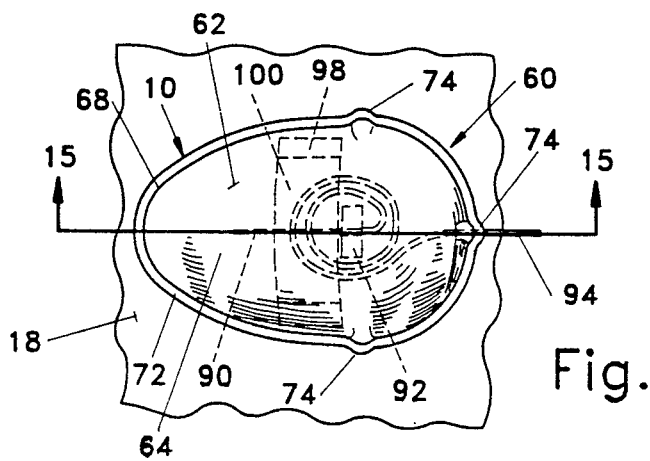
Fig. 14

NEEDLE SHIELD WITH TRANSPARENCY MAINTAINING COATING

This is a continuation-in-part application of copending application having Ser. No. 07/345,286 filed May 1, 1989, now abandoned.

BACKGROUND OF THE INVENTION

1. Field of the Invention

This invention relates to a shielding device and method for holding and protecting an infusion needle, such as a catheter, during intravenous feeding operations and the like. More particularly, this invention provides a shielding device, preferably a transparent shielding device, and method for holding and protecting a heparin lock that typically includes a catheter. This invention also provides a method for treating an inside surface of a transparent wall of a shielding device, which is for protecting an infusion needle disposed through a body portion and into a vein of a patient, such that the transparent wall generally remains transparent when the shielding device is disposed to an external surface of a body portion of a patient.

2. Description of the Prior Art

A patentability investigation was conducted and the following prior art U.S. Pat. Nos. were discovered: No. 3,194,235 to Cooke; No. 3,900,026 to Wagner; No. 3,901,226 to Scardenzan; No. 4,470,410 to Elliott; and No. 4,626,246 to Verdake. All of these prior art patents are fully incorporated herein by reference thereto.

SUMMARY OF THE INVENTION

The present invention accomplishes its desired objects by providing a shielding device for protecting an infusion needle disposed through a body portion and into a vein of a patient. The shielding device comprises a hollow cup having a generally planar flange and a transparent wall with an outside wall surface and an inside wall surface. The inside wall surface has a coating for preventing the formation of fog on the transparent wall such that the transparent wall will remain transparent when the shielding device covers an infusion needle inserted through a body portion of a patient. The coating of this invention includes a major proportion of a binding agent and a minor proportion of an emulsifying agent. The coating also preferably comprises a minor proportion of an agent which causes the coating to become more flexible. The coating preferably more specifically comprises from about 50 to about 99% by weight of a binding agent; from about 0.5 to about 30% by weight of an emulsifying agent; and preferably from about 0.5 to about 30% by weight of an agent (i.e., a flexibilizer agent) which causes the coating to become more flexible such that when the transparent wall of the hollow cup is bent, the coating is also easily bent or pliant. If the coating is not flexible and too brittle, bending of the transparent wall could cause the coating to crack and/or crumble away and expose the inside wall surface where the coating had previously been. The shielding device may have an aperture wherethrough a tube (e.g. a feeding tube, a catheter tube, a heparin lock set tube) may pass and/or slidably lodge. The shielding device may also have one or more openings wherethrough air, vapor and the like may pass to prevent fog and/or droplet condensation on the inside wall surface. The one or more openings are covered with a sheet member that is permeable to air and/or vapor while preventing the influx, or the otherwise passage, of liquids (e.g. water) through the one or more openings.

The present invention further accomplishes its desired objects by broadly providing a method for treating a shielding device such that a transparent wall of the shielding device will remain transparent, especially when disposed over an infusion needle or tube that pierces a body portion of a patient. The method for treating the shielding device comprises mixing together under ambient conditions a solvent (or carrier fluid), a binding agent, an emulsifying agent and preferably a flexibilizer agent such that all components dissolve into a mixture or solution comprising: from about 65% to about 99.4% by weight of a solvent; from about 0.4% to about 40% by weight of the binding agent; from about 0.1% to about 10% by weight of the emulsifying agent; and preferably from about 0.1% to about 15% by weight of the flexibilizer agent. The mixture is applied to the transparent wall of the shielding device and is allowed to dry into a flexible transparent anti-fogging coating that maintains the transparency of the transparent wall of the shielding device, especially when the shielding device is mounted to an external surface of a body portion of a patient to totally enclose a catheter or the like.

The binding agent is preferably an alcohol and/or water soluble polymer and/or biopolymer that is capable of binding and stabilizing the coating to form a hard and transparent film. Preferably, the binding agent is a pyrrolidone based polymer such as polyvinylpyrrolidone $(C_6H_9NO)n$ having an average molecular weight of from about 5,000 to about 5,000,000. The emulsifying agent is preferably a nonionic emulsifying agent that is capable of reducing surface tension when dissolved in water or alcohol (or water solutions or alcohol solutions) or which reduces interfacial tension between two liquids (e.g. water and an alcohol), or between a liquid (e.g. water) and a solid (such as the inside wall surface of the wall). Preferably, the emulsifying agent is an alkylphenoxypolyethoxyethanol emulsifier having an average of from about 1 to about 100 ethylene oxide units or segments and wherein the alkyl radical contains from about 8 to about 21 carbon atoms. The flexibilizer agent that causes the coating to become more flexible is preferably a polyhydric alcohol such as glycerol. The solvent is preferably an alcohol and/or an aqueous medium such as water.

The present invention still further accomplishes its desired objects by providing a device for holding a heparin lock secured to a catheter means that has been previously disposed through a body portion and into an artery of a patient. The device comprises a hollow generally elongated cover having a transparent wall constructed of generally flexible material with the transparent wall terminating to form an opening that generally circumscribes the catheter means, especially the point of entry of the catheter means into the body portion of the patient. The wall terminates in a generally continuous periphery that forms the opening and is supported on an external surface of the body portion. The wall of the elongated cover comprises a face having a continuous periphery and an aperture off-set from the periphery. Preferably, the periphery has a pair of side edges, a top edge and a bottom edge. The wall additionally includes a generally oval-shaped body integrally secured to the face along a substantial portion of the periphery and tapering rearwardly and downwardly therefrom. In a preferred embodiment where the periphery includes a pair of side edges, a top edge and a bottom edge, the oval-shaped body is integrally secured to the face at the pair of side edges and the top edge. The oval-shaped body terminates in a pair of opposed, generally parallel body edges. Integrally bound to the oval-shaped body is a rear body segment that tapers rearwardly and downwardly from the oval-shaped body to terminate in a pair of rear body edges. The rear body edges meet in a rear body apex. A pair of body flanges is secured to and extends away from the parallel body edges. The device also preferably comprises a pair of rear body flanges secured to and extending away from the rear body edges. The face of the wall slants towards the oval-shaped body commencing from a lowermost peripheral edge thereof, such as the bottom edge. A facial flange is secured to and extends away from the lowermost peripheral edge.

The present invention yet further accomplishes its desired objects by providing a method for holding a heparin lock secured to a catheter that has been disposed through a body portion and into an artery of a patient. The method comprises the steps of forming a hollow generally elongated cover having a transparent wall constructed of generally flexible material with the transparent wall terminating in a generally continuous periphery which forms an opening that is of sufficient perimeter to circumscribe the catheter, especially the point of entry of the catheter into the body portion of the patient. The wall of the elongated cover comprises a face including a continuous periphery and an aperture off-set from the periphery. Additionally, the hollow generally elongated cover is preferably formed such that a generally oval-shaped body integrally secures to the face along a substantial portion of the periphery and tapers rearwardly and downwardly therefrom. The method further comprises disposing the generally continuous periphery of the opening of the wall around a catheter that has been previously inserted or otherwise disposed through a body portion at a body entry point and into an artery of a patient; and subsequently inserting a heparin lock means into the aperture to substantially seal off the aperture. Typically, the heparin lock has the catheter secured thereto. The method further comprises securing the cover to an external surface of the body portion such that the generally continuous periphery substantially rests on the external surface of the body portion in a surrounding relation to the body entry point with the body entry point generally being in a plane that is common with a plane on and/or along the generally continuous periphery in order to totally enclose the catheter while the heparin lock remains slidably lodged within the aperture and completely sealing off the aperture.

Thus, it is an object of the present invention to provide a shielding device.

It is another object of the present invention to provide a coating; a method for treating a shielding device; and a method for holding a heparin lock that is secured to a catheter means.

These, together with the various ancillary objects and features which will become apparent to those skilled in the art as the following description proceeds, are attained by this novel device and method, a preferred embodiment being shown with reference to the accompanying drawings, by way of example only, wherein:

BRIEF DESCRIPTION OF THE DRAWINGS

FIG. 12 is a schematic view of the device of this invention covering the catheter while securing and retaining a heparin lock;

FIG. 13 is a perspective view of another embodiment of the device of this invention displaced from the feeding area with its assembled operating position on the body portion of a patient indicated by dashed lines;

FIG. 14 is a top plan view of the device of FIG. 13 disposed in covering relation to an infusion needle and supply hose on a fragmentary representation of a body portion of a patient;

FIG. 15 is a longitudinal vertical sectional view taken in direction of the arrows and along the plane on line 15—15 in FIG. 14;

DETAILED DESCRIPTION OF THE INVENTION

Figure 1:
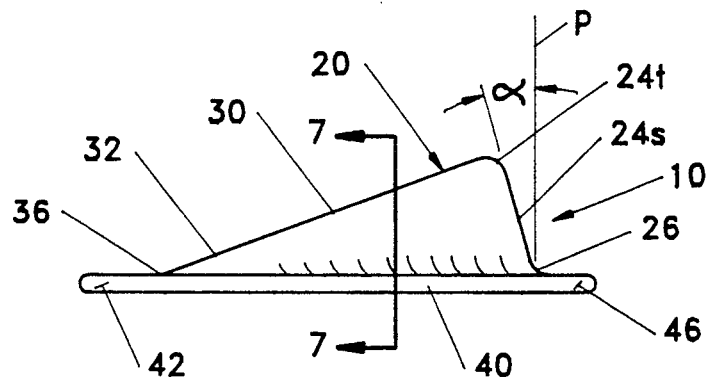
FIG. 1 is a side elevational view of one embodiment of the device of this invention.

Referring in detail now to the drawings and initially more particularly to FIGS. 1-12, wherein similar parts of the invention are identified by like reference numerals, there is seen a device, generally illustrated as 10, for holding and protecting a heparin lock 12 having secured thereto a catheter head 17 with a catheter 14. An anchor member 16 is provided to tightly mount or anchor the catheter head 17-heparin lock 12 to or against a body portion 18 of a patient. The device 10, as will be described in more detail below, is particularly suited for assisting the prevention of water and other contaminating or infecting matter from contacting the zone of the body portion 18 where the catheter 14 enters or pierces the body portion 18 of the patient. Furthermore, by keeping water and moisture away from the anchor member 16, the anchor member 16 will keep dry and will not become dislodged or unmounted from against the body portion 18. The device 10 mounts to an external surface 19 of the body portion 18 and allows a patient to take a bath or shower with the catheter 14-catheter head 17-heparin lock 12 remaining firmly planted against the external surface 19 of the body portion 18 and with reduced fears of infecting or otherwise disturbing the body portion 18. An exposed catheter head 17-heparin lock 12 may be easily jarred, bumped, and loosened by inadvertent movement of the patient or by accidental contact with an object. Serious injury may result by movement of the catheter within the artery, vein, or the like. Whenever "artery" is stated hereafter, including in the claims, it is to be construed to mean "artery, vein, or the like".

Figure 3:
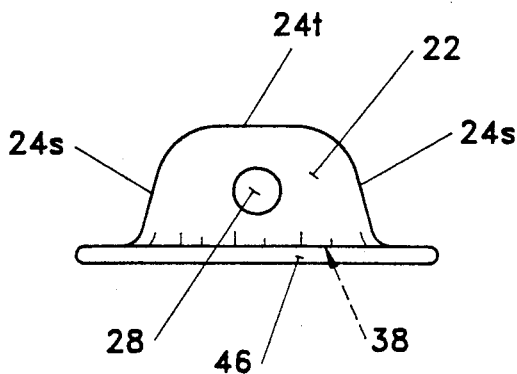
FIG. 3 is a front elevational view of the device of FIG. 1.
Figure 4:
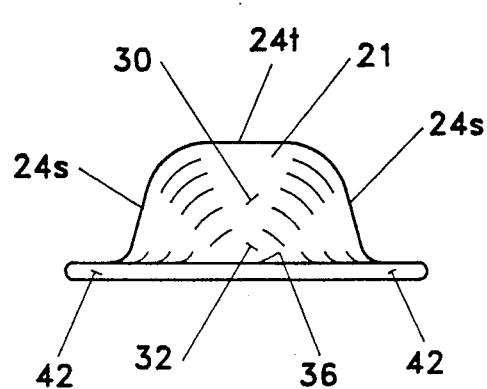
FIG. 4 is a rear elevational view of the device of FIG. 1.
Figure 5:
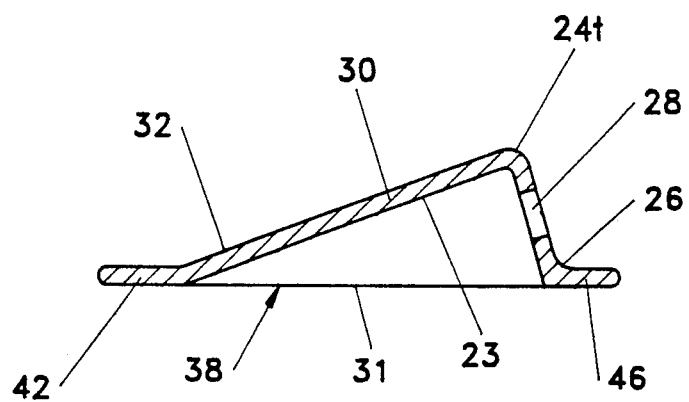
FIG. 5 is a vertical sectional view taken in direction of the arrows and along the plane on line 5—5 in FIG. 2.
Figure 10:
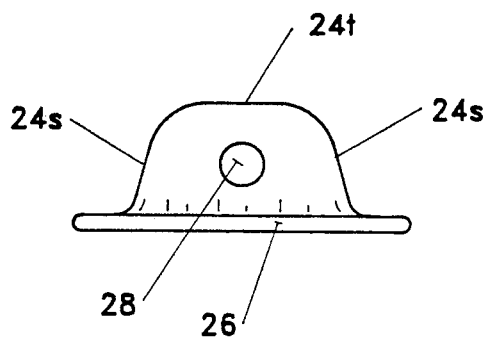
FIG. 10 is a front elevational view taken in direction of the arrows and along the plane on line 10—10 in FIG. 9.
Figure 11:
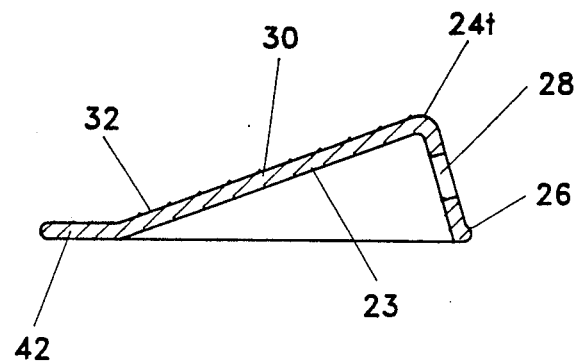
FIG. 11 is a vertical sectional view of the device of FIG. 9.

The device 10 embodying the principles of the present invention provides a hollow elongated cover or unitary construction having a wall, generally illustrated as 20, constructed of flexible material, such as lightweight plastic, lightweight rubber, or like material. Preferably, the material is transparent, waterproof and impermeable to keep moisture and germs or other infectious organisms away from the catheter 14-heparin lock 12. The wall 20 has an outside surface 21 and an inside surface 23, and is formed with a face 22 having a pair of perimetrical side edges 24s—24s joining smoothly into a perimetrical top edge 24t. As best illustrated in FIGS. 3 and 10, the perimetrical side edges 24s—24s and perimetrical top edge 24t continuously join to render face 22 with a somewhat oval shape. It is to be understood that the invention is not to be limited to a face 22 having the somewhat oval shape, but is to include semi-circular shaped faces 22, rectangular shaped faces 22, etc. Obviously, in the embodiment where the face 22 is semi-circular, perimetrical side edges 24s—24s and perimetrical top edge 24t would each define 60 degree arcs of the semi-circular face 22. The face 22 terminates at the bottom thereof in a perimetrical bottom edge 26 which joins to the pair of perimetrical side edges 24s—24s.

One of the features of the present invention is that the joined perimetrical side edges 24s—24s, the perimetrical top edge 24t and the perimetrical bottom edge 26 provide a continuous boundary or periphery for face 22. There are no openings, slots, or the like interrupting any of the edges, especially the perimetrical bottom edge 26. The only opening in face 22 is aperture 28 wherethrough the heparin lock 12 slidably passes for being held in place therein. Another feature of the present invention is that face 22 slopes or slants at an angle α (see FIG. 1) away from a vertical or perpendicular or normal plane p. The angle α is preferably from about 1 degree to about 35 degrees. This feature facilitates the lodging of the heparin lock 12 into the aperture 28.

Figure 2:
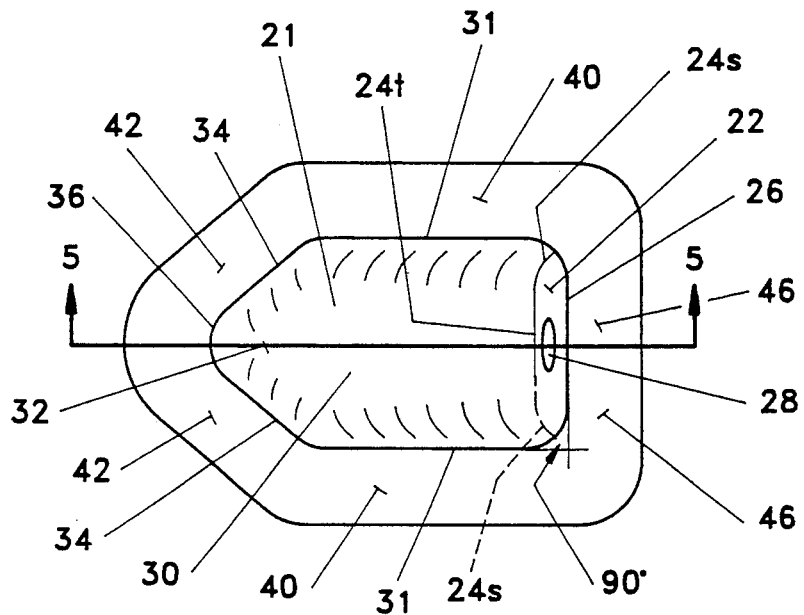
FIG. 2 is a top plan view of the device of FIG. 1.
Figure 6:
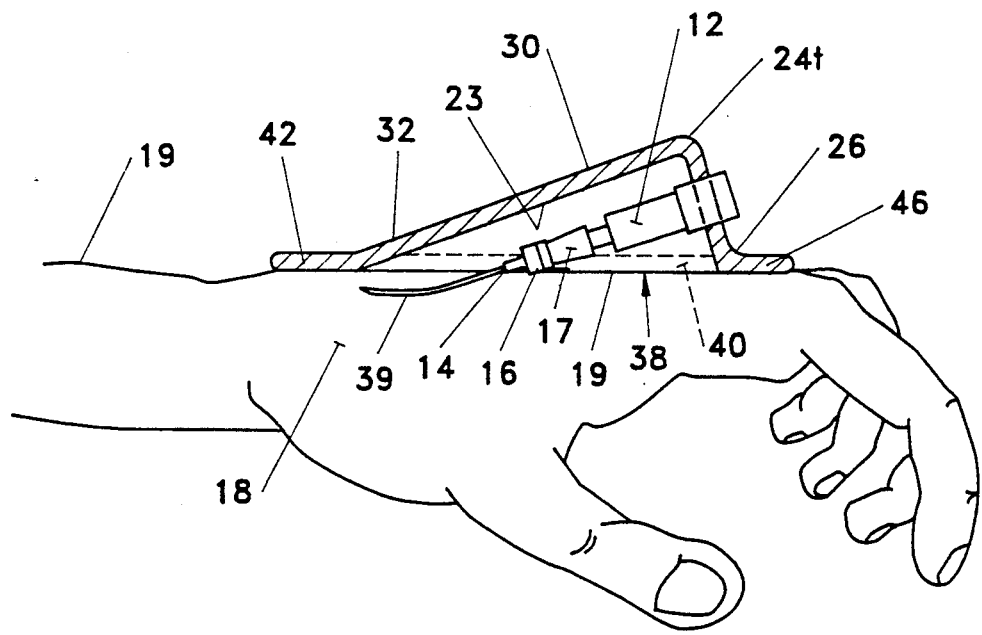
FIG. 6 is a vertical cross sectional view of the device of this invention covering the catheter while securing and retaining a heparin lock.
Figure 7:
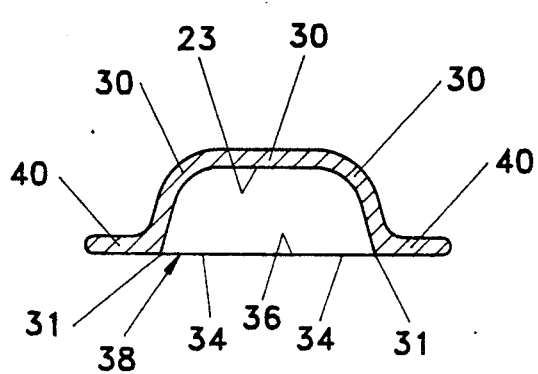
FIG. 7 is a vertical sectional view taken in direction of the arrows and along the plane of line 7—7 in FIG. 1.
Figure 8:
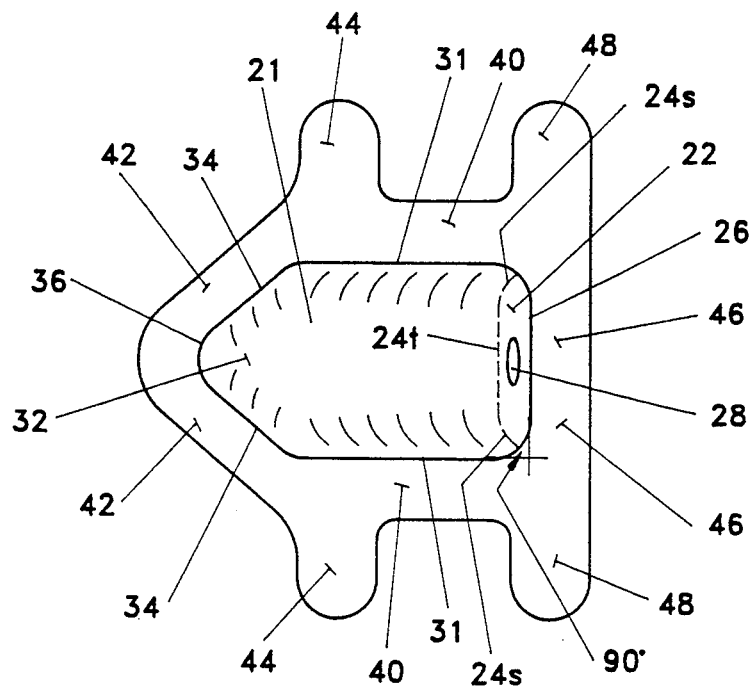
FIG. 8 is a top plan view of another embodiment of the device of the present invention.
Figure 9:
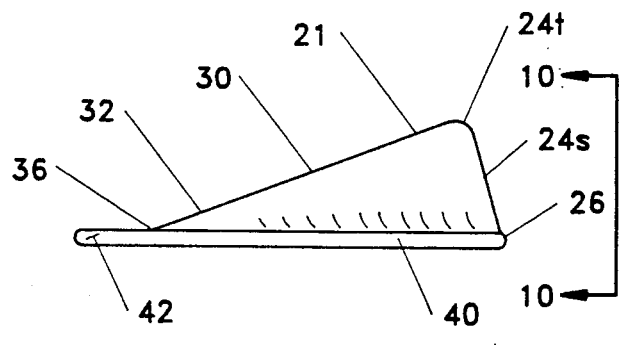
FIG. 9 is a side elevational view of yet another embodiment of the device of the present invention.

The wall 20 is also formed with a generally oval-shaped body 30 that tapers rearwardly and downwardly from the perimetrical side edges 24s—24s and the perimetrical top edge 24t, and terminates in a pair of opposed, generally parallel body edges 31—31 and a rear body segment 32 integrally, unitarily formed with the oval-shaped body 30 and comprising a pair of rear body edges 34—34 meeting in a rear body apex 36. Body edges 31—31 join and/or continue into rear body edges 34—34 and arcuately meet with the perimetrical bottom edge 26 such that a generally 90 degree angle (as best illustrated in FIGS. 2 and 8) is formed by a line or plane on or along a body edge 31 with a line or plane on or along perimetrical bottom edge 26. The bottom edge 26, the parallel body edges 31—31, the rear body edges 34—34 and the rear body apex 36 form an opening, generally illustrated as 38, which would generally circumscribe and/or surround the catheter 14, especially at a point of entry 39 (see FIG. 6) of the catheter 14 into the body portion 18 of the patient. Stated alternatively, the wall 20 terminates in the edges which form a generally continuous periphery or perimeter that defines the opening 38 which surrounds the catheter 14 when the device 10 is disposed over the catheter 14 as shown in FIG. 6. The entry point 39 is generally in the plane of a plane on and/or along the opening 38, more particularly in a plane on and/or along all of the edges (i.e., edges 26, 31—31, 34—34, and 36). When the device 10 is secured and/or mounted on or to the external surface 19 of the body portion 18, the generally continuous periphery substantially rests on the external surface 19 in a surrounding relation to the entry point 39 with the entry point 39 generally being in a plane that is common or identical with a plane along the generally continuous periphery.

A pair of generally parallel body flanges 40—40 extend away and out respectively from the parallel body edges 31—31 as best shown in FIGS. 2 and 8. Similarly, a pair of rear body flanges 42—42 extend away and out respectively from the rear body edges 34—34. Rear body flanges 42—42 meet along a plane through and bisecting rear body apex 36, and join in a continuous manner and integrally into or with body edges 31—31. In a preferred embodiment for the device 10 depicted in FIG. 8, body edges 31—31 are each formed with a body ear 44.

In a preferred embodiment of the invention, a facial flange 46 extends outwardly from the perimetrical bottom edge 26, and joins and interconnects in an integral continuous manner with and into the body flanges 40—40 as best illustrated in FIG. 2. In a preferred embodiment of the device in FIGS. 9, 10 and 11, there is no facial flange 46. In FIG. 8, the facial flange 46 is formed with and is extended outwardly with a pair of opposed facial ears 48—48 which are generally parallel to and/or with the body ears 44—44.

For the preferred embodiment of the device 10 in FIGS. 1-7, the rear body flanges 42—42, the body flanges 40—40 and the facial flange 46 form a continuously flat base for the wall 20 so that the device 10 may be mounted tightly against the external surface 19 of the body portion 18 of the patient with a minimum of discomfort. Such mounting may include adhesive means (e.g. glue, etc.) disposed on the bottom of all the flanges 40—40, 42—42, and 46, or by taping the flanges against the external surface 19 of the body portion 18, or the like. In FIG. 8, body ears 44—44 and facial ears 48—48 form part of the base. For the preferred embodiment of the device 10 in FIGS. 9, 10 and 11, where there is no facial flange 46, the flanges 40—40 and 42—42 form the continuous flat base for the wall 20.

As best shown in FIG. 6 and in FIG. 12, the device 10 is adapted to be rested on the external surface 19 of the body portion 18 in the position illustrated in a covering relation to the catheter 14 and the catheter head 17 (anchored to the body portion 18 by anchor member 16) having or including the heparin lock 12 secured thereto and slidably lodging in aperture 28 of the face 22. The catheter head 17, after removing the heparin lock 12, may be connected to a supply hose (not shown) coupled with a source of infusion liquid (also not shown). As previously indicated, when the device 10 rests on the external surface 19 of the body portion 18 in an enclosing relationship to the catheter 14 (as indicated by the dotted or dashed lines in FIG. 12) and to the catheter head 17 (enclosed to the body portion 18 by anchor member 16) the point of entry 39 is generally in the plane of a plane on and/or along the opening 38; more particularly, the point of entry 39 is generally in the plane of a plane on and/or along all of the edges (i.e., edges 26, 31—31, 34—34 and 36) which is the termination point of the wall 20.

Referring now to the embodiment of the invention depicted in FIGS. 13-19, there is seen the device 10 as being a shielding device 10 for protecting any needle, catheter, tube, and/or the like, that passes into the body portion 18 of a patient. The shielding device 10 is hollow and may be of any suitable hollow geometric shape, such as a square, a rectangle, elliptical, etc. More specifically, the shielding device 10 may be any hollow member or cupped body (e.g. a rectangular or square cupped body). By way of example only and as illustrated in FIGS. 13-19, the shielding device 10 may be any bulbous, hollow cup-like device that is concave-convex in cross section (as seen particularly in FIGS. 15 and 17) and oval or pear-like in outline. Preferably, the shielding device 10 embodying the present invention provides a hollow and/or bulbous cup-like member 60 of unitary construction having a wall 62 which may be of any geometric shape and fashioned from any material, such as rubber, lightweight metal, plastic (e.g. polyvinyl chloride), etc. Injection molding and thermoforming are among the suitable processes by which the cup-like member 60 including the wall 62 can be manufactured, especially when the cup-like member 60 including the wall 62 is fashioned from any suitable plastic material (e.g. PVC, polyethylene, etc.) which may or may not be transparent. Preferably, the cup-like member 60 including the wall 62 is transparent. Transparency is important since the shielding device 10 functions not only as an enclosure but also as a window through which visual inspection may be made of any arterial catheter (or tube, etc., or the like), the entrance of the catheter into the body, and the condition of the skin surface immediately around the arterial catheter.

The wall 62 has an outside surface 64 and an inside surface 66. The wall 62 terminates in a perimetrical or marginal edge 68 which is contoured to any shape or size, depending on the size and shape of the cup-like member 60 including the wall 62. The perimetrical or marginal edge 68 forms a generally continuous perimeter of an opening, generally illustrated as 70, wherein the any catheter (or tube, needle, etc., or the like) resides as will be further explained below. A plane on and/or along the marginal edge 68 would generally include a plane across the opening 70. A continuous integral flange 72 is extended outwardly from the marginal edge 68 to form a substantially flat base or foundation for the wall 62 so that the shielding device 10 may be mounted tightly and comfortably against the external surface 19 of the body portion 18 of the patient. The structure of the. integral flange 72 may advantageously include a plurality of spaced marginal indentations or arcuate elevated portions 74 wherethrough a tube, a hose, or the like, passes as shown in FIG. 15. The shielding device 10 in FIG. 17 has no arcuate elevation portions 74 but includes an aperture 76 wherethrough a tube, catheter, needle or the like passes. The aperture 76 may be employed in combination with arcuate elevated portions 74 as shown in the shielding device 10 illustrated in FIG. 16.

Figure 18:
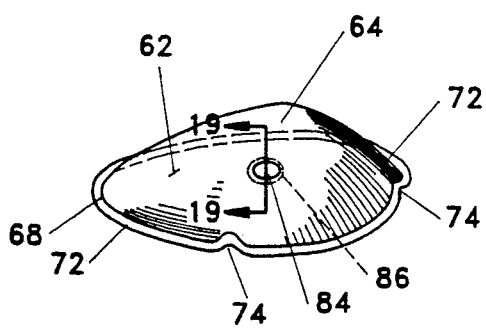
FIG. 18 is a perspective view of still yet another embodiment of the device of the invention.
Figure 16:
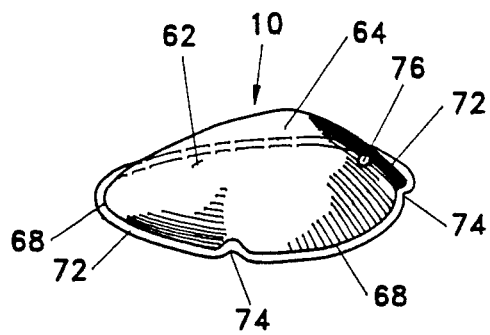
FIG. 16 is a perspective view of yet another embodiment of the device of this invention.
Figure 19:
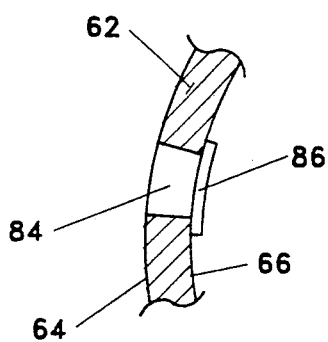
FIG. 19 is a partial vertical sectional view taken in direction of the arrows and along the plane on line 19—19 in FIG. 18.
Figure 17:
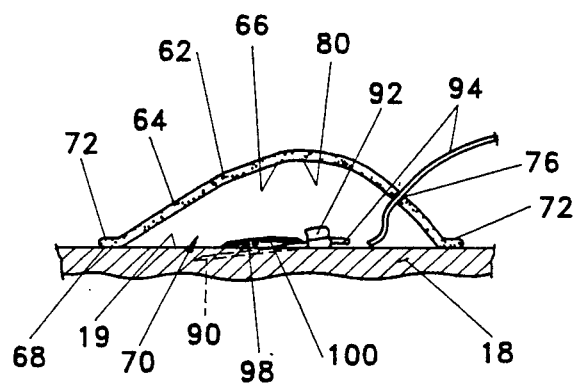
FIG. 17 is a longitudinal vertical sectional view of the device of FIG. 16 in covering relation to a needle and a tube or supply hose with the tube or supply hose extending through an aperture in the wall of the device.

In one embodiment of the shielding device, 10 of FIGS. 13-19, a coating 80 is disposed on (or otherwise secured to or bonded thereon) the inside surface 66 of the wall 62 as best shown in FIGS. 15 and 17. The coating 80 (or layer or film) is an anti-fogging composition and maintains the transparency of a transparent wall 62. The coating 80 also prevents the formation of condensation droplets emanating from the air when the shielding device 10 covers a catheter, needle, tube, or the like, that passes through the body portion 18 of a patient. In another embodiment of the shielding device 10, an opening 84 is provided in the wall 62 to ventilate the interior of the shielding device 10 to further prevent fogging of a transparent wall 62 and to permit the body portion 18 to "breathe" when the shielding device 10 is disposed over a needle or catheter and mounted against the external surface 19 of the body portion 18. A sheet member 86 is connected to or bound to the inside surface 66 of the wall 62 to cover the opening 84. The sheet member 86 is permeable to air and/or vapor, but is impermeable to liquids, such as water. The air permeable sheet member 86 allows ventilation of the interior of the shielding device 10 to assist in preventing fogging of the transparent wall 62 and also to assist in allowing the covered body portion 18 to "breathe" and receive oxygen from the air. As best shown in FIG. 15, the sheet member 86-covered opening 84 embodiment may be employed in combination with the coating 80 on the inside surface 66. Alternatively, the coating 80 on the inside surface 66 may be employed alone and without the wall 62 having a sheet member 86-covered opening 84 as shown in FIG. 17. Similarly, as best illustrated in FIGS. 18 and 19, the sheet member 86-covered opening 84 embodiment may be used without the inside surface 66 having the coating 80.

The shielding device 10 is adapted to be rested on the external surface 19 of the body portion 18 of a patient in the position illustrated in FIGS. 15 and 17 and further illustrated by a dashed or dotted line 89 in FIG. 13, to cover any tubes, needles, catheters, or the like, to a medical patient's body including feeding tubes, mesentary tubes, naso-gastric tubes, chest tubes, catheters such as foley catheters as well as condom catheter tubes, dialysis tubes, angiocath and heparin lock set tubes, as well as other tubes, needles, etc., and the like used to introduce fluids into the body intraveneously or to introduce oxygen into the mouth or nose of a medical patient. By way of example only and as illustrated in FIGS. 13, 14, 15 and 17, a needle 90, including a handle 92 that is connected to a tube or hose 94 with an extended connecting end 96 which is adaptable to be coupled with a source of infusion liquid, is. inserted into a blood vessel in the body portion 18 of the patient. The needle 90 may be constrained by a strip of adhesive tape or the like 98. The supply tube 94, which is connected to the handle 92 of the needle 90, may be advantageously coiled into a substantially flat coil around the handle 92 as best shown in FIG. 13. A second strip of adhesive 100 may be employed to secure the substantially flat coil in an overlaying relationship to the strip of adhesive tape 98. The shielding device 10 is subsequently disposed in a covering relation to the needle 90 (and its associated handle 92 and connected tube 94) in the dashed line position 89 of FIG. 13. In such a posture, the supply tube 94 may be extended outwardly from the cup-like member 60 either through aperture 76 (see FIGS. 16 and 17), or through one of the arcuate elevated portions 74 in the flange 72. The shielding device 10 may be held in covering relation to the needle 90 by any suitable means, such as an adhesive tape (not shown) over the shielding device 10 and releasably securing to the external surface 19 of the body portion 18, or an adhesive tape (not shown) over the flange 72 and releasably securing to the external surface 19 of the body portion 18, or undercoating the integral flange 72 with any suitable adhesive means for releasably securing the shielding device 10 including the flange 72 to the external surface 19 of the body portion 18. The body portion 18 of the medical patient covered by the shielding device 10 is permitted to "breath" by way of opening 84 that is covered with the air permeable sheet member 86. For a transparent wall 62, the opening 84 in the wall 62 and covered with the air permeable sheet member 86 ventilates the inside(s) of the cup-like member 60 such that the transparent wall 62 remains transparent and does not fog or otherwise become somewhat non-transparent such as by condensation droplet formation. It is clearly apparent that an air permeable sheet member 86 may be secured to either the outside surface 64 and/or to the inside surface 66 by any suitable adhesive means, such as glue, etc. The coating 80 undercoated to the inside surface 66 of the wall 62 is an anti-fogging composition of matter which maintains the transparency of a transparent wall 62 and further prevents condensation droplets forming on the inside surface 66 of the wall 62. Droplets of condensation can hinder the transparency of a transparent wall 62.

Figure 20:
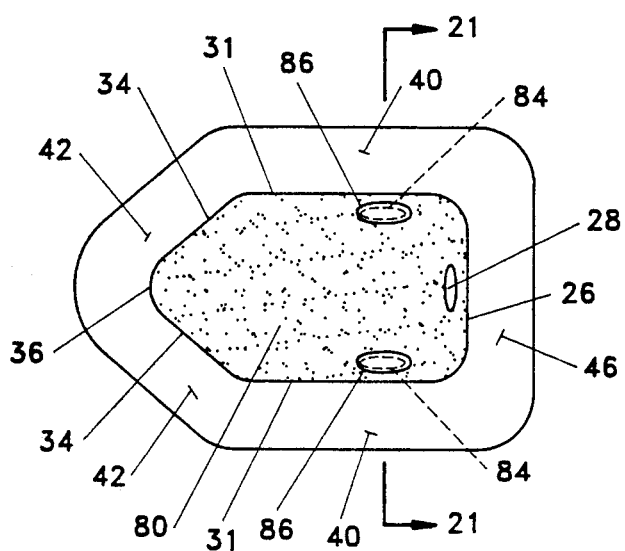
FIG. 20 is a bottom plan view of the device of FIGS. 1-7 modified to have a coating to maintain the walls transparent and an opening in the walls that is covered with an air permeable sheet member.
Figure 21:
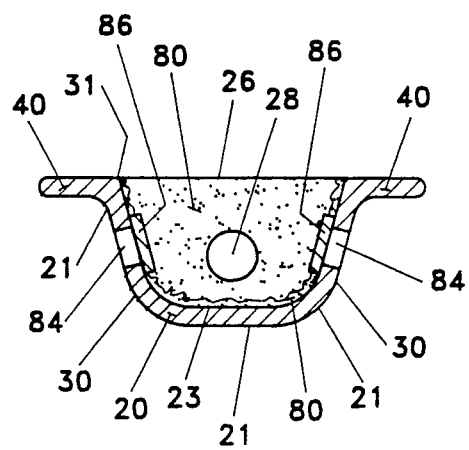
FIG. 21 is a vertical sectional view taken in direction of the arrows and along the plane on line 21—21 in FIG. 20.
Figure 22:
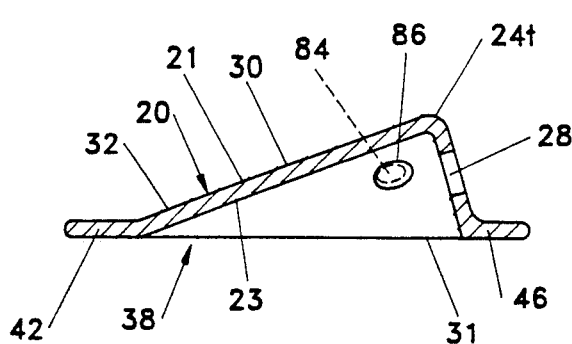
FIG. 22 is a longitudinal vertical sectional view through the device of FIGS. 1-7 modified to have an opening in the walls and wherein the opening is covered with an air permeable sheet member.
Figure 23:
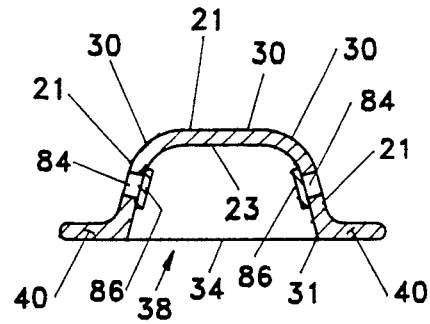
FIG. 23 is a transverse vertical sectional view through the device of FIGS. 1-7 modified to have a pair of openings in the walls thereof and wherein the pair of openings are each covered with an air permeable sheet member.
Figure 24:
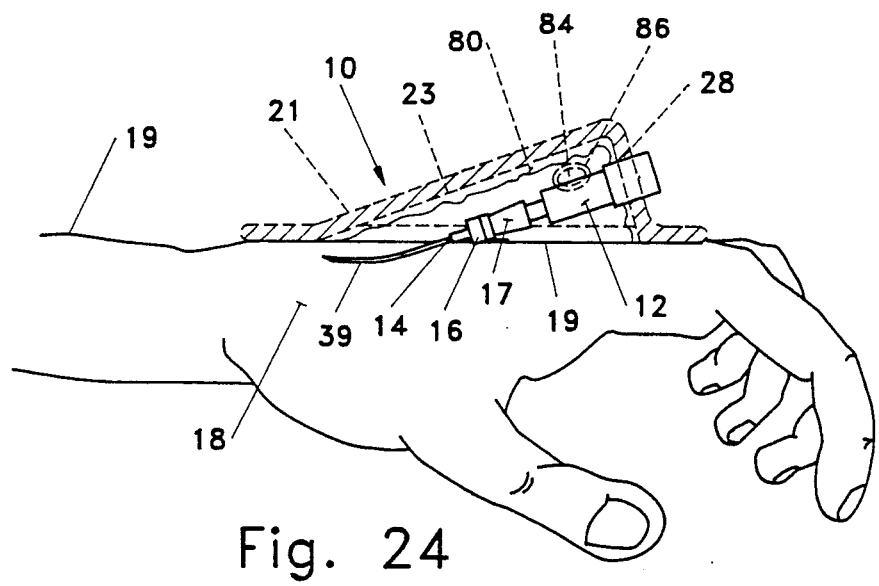
FIG. 24 is a schematic view of the device having a coating on the inside surface thereof and an opening in the wall thereof which opening is covered by an air permeable sheet member, and in covering relation to a catheter while securing and retaining a heparin lock.

The preferred embodiment of the invention previously described and as depicted in FIGS. 1-12 may include the coating 80 of this invention and may be provided with at least one opening 84 for use of the sheet member 86 of this invention. More specifically, and as best shown in FIGS. 20, 21 and 24, the inside surface 23 of wall 20 may be coated or layered with the coating 80. The face 22 and the oval-shaped body 30 are undercoated with the coating 80. As best shown in FIGS. 20-24 the oval-shaped body 30 has the opening 84 that is covered with the air permeable sheet member 86. The air permeable sheet member 86 ventilates, decondensates and allows the inside of the device to "breathe" and aerate, while keeping water and other fluids out such as when a patient takes a shower or a bath. In covering the opening 84, the air permeable sheet member 86 can be connected to the inside surface 23 or to the outside surface 21 or to both by any suitable adhesive or bonding means. The coating 80 may be disposed on all or a portion of the inside surface 23 such that a transparent wall 20 remains transparent. As previously mentioned, the device 10 may only include an opening 84 covered with the air permeable sheet member 86 and not undercoated (see FIGS. 22-23); or the device 10 may include only the coating 80 and no opening 84 covered with air permeable sheet member 86; or the device 10 may include the combination of the coating 80 and one or more opening(s) 84 covered with one or more air permeable sheet member 86 (as shown in FIGS. 20, 21 and 24).

Figure 25:
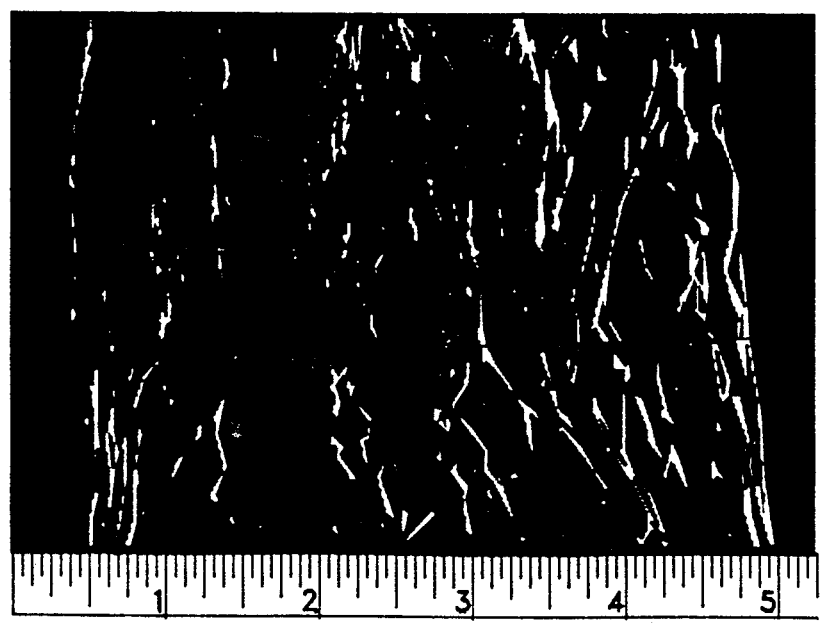
FIG. 25 is a schematic view of a sheet of a spunbonded olefin sold under the trademark TYVEK ® registered to the DuPont Co. and disclosing the fiber structure of the spunbonded olefin.

The sheet member 86 of this invention may be any sheet member that is capable of permitting air, vapor, and moisture (i.e., highly humid air) to pass or permeate therethrough while being essentially impenetrable to fluids (e.g. water). Preferably, the sheet member 86 is manufactured from a spunbonded olefin that is sold commercially under the trademark TYVEK ® which is registered to the DuPont Co. TYVEK ® spunbonded olefin is a family of tough, durable sheet products of high-density polyethylene fibers. The sheet is formed by first spinning continuous strands of very fine, interconnected fibers and then bonding them together with heat and pressure. FIG. 25 shows the fineness of the fibers making up a strand. The sheet, after bonding, combines a good printing or coating surface, high opacity, and toughness.

TYVEK ® spunbonded olefin is produced in three different types, namely, 10, 14 and 16. The fibers in Type 10 styles are bonded to form a tough, dense, opaque sheet. The dense packing of the fine, interconnected fibers produces a smooth surface, high opacity, and good whiteness. The large number of bonds per unit area results in a stable and abrasion-resistant surface, yet the bonded fibers retain enough mobility to give the sheet high tear strength in all directions. Physical property data for various Type 10 styles are summarized in the following Table I:

TABLE I

| | TYPICAL PROPERTIES OF TYVEK ® TYPE 10 SPUNBONDED OLEFIN | | | | | | | |
|---|---|---|---|---|---|---|---|---|
| | Style 1056D | Style 1058D | Style 1059B | Style 1073D | Style 1073B | Style 1079D | Style 1079K | Style 1085D |
| Basis Weight oz./yd.$^2$ (g/m$^2$) | 1.6 (54.3) | 1.6 (54.3) | 1.8 (61) | 2.2 (74.6) | 2.2 (74.6) | 2.95 (100) | 2.70 (91.6) | 3.25 (110.2) |
| Thickness, mils (mm) | 6.5 (0.17) | 6.0 (0.15) | 6.7 (0.17) | 8.0 (0.20) | 8.0 (0.20) | 9.5 (0.24) | 7.5 (0.19) | 10.0 (0.25) |
| Breaking Strength (Strip Test) | | | | | | | | |
| lbs./in. (MD/XD)* | 27/33 | 31/36 | 36/43 | 45/53 | 45/53 | 63/76 | 63/75 | 68/80 |

TABLE I-continued

| TYPICAL PROPERTIES OF TYVEK ® TYPE 10 SPUNBONDED OLEFIN | | | | | | | | |
|---|---|---|---|---|---|---|---|---|
| | Style 1056D | Style 1058D | Style 1059B | Style 1073D | Style 1073B | Style 1079D | Style 1079K | Style 1085D |
| (N/cm) | (47/58) | (54/63) | (63/75) | (79/93) | (79/93) | (110/133) | (110/131) | (119/140) |
| Elongation to break % (MD/XD) | 21/27 | 24/30 | 26/31 | 26/33 | 26/33 | 30/36 | 33/41 | 29/35 |
| Elmendorf Tear Lbs. (MD/XD) | 1.0/1.0 | 0.7/0.8 | 0.9/0.9 | 1.0/1.0 | 1.0/1.0 | 1.1/1.1 | 0.8/0.8 | 1.2/1.2 |
| (N) | (4.5/4.5) | (3.1/3.6) | (4/4) | (4.5/4.5) | (4.5/4.5) | (4.9/4.9) | (3.6/3.6) | (5.3/5.3) |
| MIT Flex, cycles | >100M† | >100M | >100M | >100M | >100M | >100M | >100M | >100M |
| Eddy Opacity, %** | 90 | 82 | 85 | 88 | 88 | 89 | 79 | 90 |
| Gurley Porosity, †† seconds | | | 20 | | 23 | | | |
| Water Vapor Permeability g/m².24 hr. | 694 | 688 | 684 | 614 | 641 | 636 | 522 | 647 |
| Mullen Burst lbs./in.² (kPa) | 104/(717) | 114 (786) | 155 (1070) | 201 (1385) | 171 (1180) | 241 (1660) | 226 (1560) | 267 (1840) |

*MD is Machine Direction; XD is Cross Machine Direction
**100% is opaque
†M = thousand
†† s/100 cm³ of air/in.² (~16 cm³/cm²)

Fiber bonding of Types 14 and 16 is restricted to discrete points in the sheet, thus producing a high degree of fiber mobility in the sheet, and giving it a fabric-like drape. Like Type 10 styles, Types 14 and 16 have high opacity, good whiteness, and a high level of surface stability. They also have higher tear strengths (weight for weight), but lower breaking strengths and surfaces less smooth than Type 10. Type 16 styles are also pin-hole perforated, which gives them much higher air and moisture permeability, additional softness, and still better flexibility and drape than Type 14 styles. Physical property data for various Type 14 and 16 styles are summarized in the following Table II:

cent in processing by using heat or pressure to remove the air, or by filling the air spaces with various clear resins, polymers, or oils. In the present invention, it is not necessary that the sheet member 86 be transparent or translucent.

The coating 80 which is connected to or otherwise bonded to the inside wall of the device 10 may be any suitable coating, film, layer or the like which functions as an anti-fogging composition to prevent the transparent wall (i.e., wall 20 and/or wall 62) of the device lo from fogging and/or otherwise becoming non-transparent such as from and through condensation droplet formation. It is believed that in the event that any mois-

TABLE II

| TYPICAL PROPERTIES OF TYVEK ® TYPES 14 & 16 SPUNBONDED OLEFIN | | | | | | | | |
|---|---|---|---|---|---|---|---|---|
| | Style 1422A/R | Style 1443R | Style 1444S | Style 1445A | Style 1458 | Style 1622E | Style 1658 | Style 1421F** |
| Basis Weight oz./yd.² (g/m²) | 1.15 (39) | 1.25 (42.4) | 1.25 (42.4) | 1.35 (45.8) | 1.6 (54.3) | 1.15 (39) | 1.6 (54.3) | 1.2 (41) |
| Thickness, mils (mm) | 5 (0.13) | 6 (0.15) | 6 (0.15) | 6 (0.15) | 7 (0.18) | 6 (0.15) | 7 (0.18) | 5 (0.13) |
| Breaking Strength (Strip Test) lbs./in. (MD/XD)* | 7.0/9.0 | 8.0/11 | 4.5/4.5 | 9.0/12 | 9.5/13 | 6.0/8.0 | 9.2/12 | 5.5/8.0 |
| (N/cm) | (12/16) | (14/19) | (8/8) | (16/21) | (17/23) | (11/14) | (16/21) | (10/14) |
| Tongue Tear lbs. (MD/XD) | 1.9/2.1 | 2.1/2.1 | 1.5/1.5 | 2.3/2.5 | 2.5/2.6 | 1.5/1.7 | 2.7/2.8 | 1.9/2.1 |
| (N) | (8.5/9.3) | (9.3/9.3) | (6.7/6.7) | (10.2/11.1) | (11.1/11.6) | (6.7/7.6) | (12/12.5) | (8.5/9.3) |
| MIT Flex, cycles | >100M† | >100M | >100M | >100M | >100M | >100M | >100M | >100M |
| Mullen Burst lbs./in.² (kPa) | | 50 (345) | | 60 (414) | | | | 40 (276) ) |
| Frazier Porosity ft.³/ft.²/min. | <1 | <1 | <1 | <1 | <1 | 45 | 40 | <1 |
| (dm³/m²/s) | (<5) | (<5) | (<5) | (<5) | (<5) | (230) | (200) | (<5) |

*MD is Machine Direction; XD is Cross Machine Direction
**Coated product
†M = thousand Compared with most textile fabrics, the air permeability of Types 10 and 14 is lower, and moisture-vapor transmission is similar to that of certain coated papers. Type 16 styles have high air permeability, comparable to that of shirting fabrics, and also high moisture-vapor transmission. Type 16 is the preferred type of TYVEK ® spunbonded olefin for the sheet member 86. Types 10, 14 and 16 all would prevent a fluid from passing through the opening 84 in the walls of the device 10. High opacity of the Types results from multiple light refractions among the very fine polyethylene fibers and air within the densely packed sheet structure; no pigments, delustrants, or whiteners are added. TYVEK ® spunbonded olefin can thus be made transluture or water forms on the inside surface (i.e., inside surface 23 and/or inside surface 66) of the wall (i.e., wall 20 and/or wall 62) of the device 10, the moisture or water remains in a layer or sheet form and does not coagulate into droplets, thus preserving the transparency of the transparent wall of the device 10. The coating 80 comprises a major proportion of a binding agent and a minor proportion of an emulsifying agent. The coating 80 also preferably comprises a minor proportion of an agent [hereinafter referred to as a "(flexibilizer) agent"] which causes the coating 80 to become more flexible. The coating 80 more particularly preferably comprises from about 50 to about 99% by weight of a binding agent; from about 0.5 to about 30% by weight of an emulsifying agent; and preferably from about 0.5 to about 30% by weight of a (flexibilizer) agent which causes the coating 80 to become more flexible and pliable such that when the transparent wall of the device 10 is bent or otherwise disturbed, the coating 80 also bends or conforms to the disturbance such as not to crumble or crack to expose the inside surface of the transparent wall of the device 10. The coating 80 more preferably comprises from about 70% by weight to about 90% by weight of the binding agent; from about 2% to about 14% by weight of the emulsifying agent; and from about 4% to about 20% by weight of the (flexibilizer) agent; most preferably from about 75% by weight to about 85% by weight of the binding agent; from about 6% to about 10% of the emulsifying agent; and from about 10% by weight to about 14% by weight of the (flexibilizer) agent.

The binding agent is any binder which would adhere to the base material of the wall of the device (e.g. such as transparent plasticized polyvinyl chloride), would be soluble in mild solvents (e.g. water and/or alcohol), would be inherently flexible or capable of being plasticized by a suitable plasticizer to become flexible, would be compatible with common emulsifying agent(s), and would provide a clear/transparent film when dry. Preferably the binding agent is an alcohol and/or water soluble polymer and/or copolymers and/or biopolymers and/or biocopolymers that are capable of binding and stabilizing the coating 80 to form a flexible and transparent film. The binding agent is preferably selected from the group consisting of pyrrolidone based polymers such as polyvinylpyrrolidone, copolymers of polyvinylpyrrolidene (PVP) such as PVP/acrylic acid and/or PVP/vinyl acetate, polyvinyl methyl ether/-maleic anhydride copolymers, polyamides, cellulose acetate butyrate, poly (ethyloxazoline), and sodium ester of carboxymethylcellulose; and mixtures thereof. The binding agent is more preferably selected from the group consisting of a pyrrolidone based polymer (such as polyvinylpyrrolidone), copolymers of polyvinylpyrrolidone PVP) (such as PVP/acrylic acid and PVP/vinyl acetate), and mixtures thereof. The binding agent is most preferably a pyrrolidone based polymer such as polyvinyl pyrrolidone (PVP) $(C_6H_9NO)_n$ having an average molecular weight of from about 5,000 to about 5,000,000. Polyvinylpyrrodidone is a white, free-flowing amorphous powder or aqueous solution, and is soluble in water, alcohol, and other organic solvents. It is compatible with a wide range of hydrophilic and hydrophobic resins, and typically has a specific gravity of 1.23 to 1.29 and a bulk density of 25 lb. per cubic foot.

PVP is manufactured in the United States in four viscosity grades identified by their Fikentschner's K-value, which approximates K-15, K-30, K-60, and K-90. The number average of the molecular weights for these grades are about 10,000, 40,000, 160,000, and 360,000, respectively.

Fikentschner's K-values may be defined by the following equation:

$$\frac{\log h_{rel}}{c} = \frac{75 K_0^2}{1 + 1.5 K_0 c} + K_0$$

$$K = 1000 K_0$$

where c=concentration in g/100 mL solution and $h_{rel}$=viscosity of the solution compared with solvent. [For a complete discussion of polyvinylpyrrolidone see *Handbook of Water Soluble Gums and Resins* (edicted by Robert L. Davidson, copyrighted in 1980 and published by McGraw Hill). Particular attention is directed to Chapter 21 of this reference which is entitled "Polyvinylpyrrolidone".]

The K-value or molecular weight is a significant determinant in the properties of a PVP product. The viscosity of a solution, obviously, increases at a fixed concentration with higher K-value resins. In addition, film and solution properties change with Fikentschner's K-value. PVP K-15, K-30, and K-90 are available as powders with a maximum of 5% water. PVP K-90 and K-60 are produced in aqueous solution with solids content of 20 and 45%, respectively.

In a preferred embodiment of the present invention, a preferred suitable polyvinylpyrrolidone polymer has been determined to be that selected from the following products sold by GAF Corporation under the group of PVP polymer product name(s): PVP K-15 (a powder having an average molecular weight of about 10,000), PVP K-30 (a powder having an average molecular weight of about 40,000), PVP K-60 (a 45% aqueous solution having an average molecular weight of about 160,000), PVP K-90 (a powder or 20% aqueous solution, having an average molecular weight of about 360,000); and mixtures thereof. More preferably, the polyvinylpyrrolidone polymer is selected from PVP K-30, PVP K-90, and mixtures thereof. A more preferred suitable polyvinylpyrrolidone polymer has been determined to be a mixture of PVP K-30 and PVP K-90, mixed in a weight ratio of from about 1 part K-30: 2 parts K-90 to about 2 parts K-30: 1 part K-90, more preferably mixed in about a 1:1 weight ratio. Stated alternatively, a more preferred suitable polyvinylpyrrolidone polymer has been determined to be a PVP polymer mixture comprising from about 33.33 wt. % to about 66.66 wt. % PVP K-30 and from about 33.33 wt. % to about 66.66 wt. % K-90, more preferably about a 50/50 wt. % mixture of PVP K-30 and PVP K-90.

The emulsifying agent(s) employed in the present invention to formulate the coating 80 may be any emulsifying agent that is capable of reducing surface tension when dissolved in water or alcohol (or water solutions or alcohol solutions) or which reduces interfacial tension between two liquids (e.g. water and an alcohol), or between a liquid (e.g. water) and a solid such as the inside wall surface of the wall of the device 10). The emulsifying agent(s) employed in the present invention may be anionic, cationic, nonionic, amphoteric and the like. Most of the inexpensive and sufficient candidates for forming the coating 80 are either anionic or nonionic. Nonionics are presently preferred because they are generally cheaper.

The best known of all the anionic-active emulsifying agents are the soaps which are the salts of the long-chain fatty acids, derived from naturally occurring fats and oils, in which the acids are found as triglycerides. The soaps used as emulsifying agents may be obtained from natural oils, in which case they will consist of a mixture of fatty acids, the precise nature or the mixture depending on the fat or oil employed. The mixed fatty acids of tallow, coconut oil, palm oil, and the like, are those commonly employed. The acids derived from tallow, for instance, may be partially separated by filtration or by pressing into "red oil" (principally oleic acid)

and the so-called "stearic acid" of commerce, which is sold as single-, double-, or triple-pressed depending on the extent to which oleic acid is separated. Such stearic acid is actually a mixture of stearic and palmitic acids.

The nonionic emulsifying agents can be classified into five types, namely, ether linkage, ester linkage, amide linkage, miscellaneous linkages, and multiple linkage. Preferred nonionic emulsifying agent(s) are those selected from the compounds having the general formula:

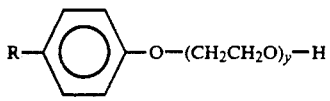
(1)

and

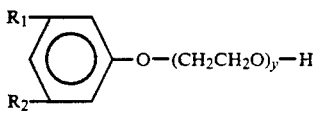
(2)

where each R, $R_1$ and $R_2$ is any hydrocarbon group, preferably an alkyl radical containing from about 8 to about 21 carbon atoms, and each of y and $y_1$ is an integer that represents the average number of ethylene oxide units or segments in the emulsifying agent(s), which is the mean of a normal Gaussian distribution curve. Preferably, each of y and $y_1$ ranges from about 1 to about 100, more preferably from about 4 to about 30.

Other preferred nonionic emulsifying agent(s) are those selected from the compounds which have the general formula:

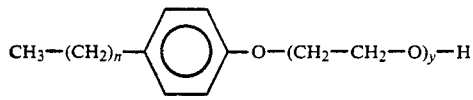
(3)

where n is from about 7 to about 20, preferably 7 to 11, and y is an integer that represents the average number of ethylene oxide units or segments in the emulsifying agent(s), which is the mean of a normal Gaussian distribution curve and is from about 1 to about 100, preferably from about 4 to about 30, more preferably from about 15 to about 20; and

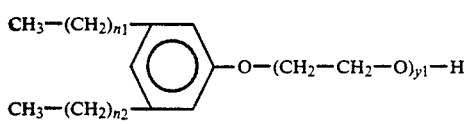
(4)

wherein $n_1$ is from about 7 to about 18, preferably 7 or 8, $n_2$ is from about 7 to about 18, preferably 7 or 8, and $y_1$ is an integer that represents the average number of ethylene oxide units or segments in the emulsifying agent(s), which is the mean of a normal Gaussian distribution curve and is from about 1 to about 100, preferably from about 4 to about 30, more preferably from about 15 to about 20.

The nonionic emulsifying agent(s) of this invention may be a combination of the compounds having the general formula (3) and the compounds having general formula (4), with the compounds having the general formula (4) being at least 40% by weight of the combination. More preferably, the compounds having general formula (4) are from about 50% by wt. to about 85% by wt. of the combination.

The most prominent members of the class of nonionic emulsifying agent(s) represented by the foregoing general formulas (1), (2), (3) and (4) are those compounds formed by the reaction of a hydrophobic hydroxyl-containing compound, e.g., an alcohol or phenol, with ethylene oxide. The ethylene oxide groups, for example, may be added to any desired extent.

The emulsifying agent(s) employed to formulate the coating 80 of the present invention can comprise emulsifying agent(s) represented by the general formula (1) and/or the general formula (2) in combination with the emulsifying agent (s) represented by the general formula (3) and/or the general formula (4). Typically, when such combination or combinations are employed, the amount or quantity of emulsifying agent(s) represented by the general formula (3) and/or the general formula (4) would comprise from about 20% by wt. to about 80% by wt. of the total amount or quantity of the emulsifying agent(s) employed within the emulsifying composition(s).

The presently nonionic emulsifying agent(s) having an ester linkage include compounds of the following general formula:

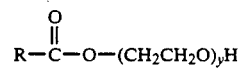

where R is any hydrocarbon group, preferably an alkyl radical containing from about 8 to about 21 carbon atoms, more preferably R is $C_8H_{17}$ or $C_9H_{19}$; and y is an integer that represents the average number of ethylene oxide units or segments in the emulsifying agent(s), which is the mean of a normal Gaussian distribution curve and is from about 1 to about 100, preferably from about 1 to 30, more preferably 10 to 25.

The esters formed by the reaction of the fatty acids with polyhydric alcohols are a particularly interesting group of nonionic emulsifiers, in that, depending on the nature of the alcohol used, they may be predominantly hydrophilic.

An example of an ester-linkage surfactant which is a good emulsifying agent is:

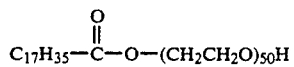

Nonionic emulsifying agent(s) with amide linkages are compounds of the general formula:

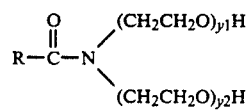

where R is any hydrocarbon group, preferably an alkyl radical containing from about 8 to about 21 carbon atoms, more preferably R is $C_8H_{17}$ or $C_9H_{19}$; and each of $y_1$ and $y_2$ is an integer that represents the average number of ethylene oxide units or segments in the emulsifying agent(s), which is the mean of a normal Gaussian distribution curve and is from about 1 to about 100, preferably from about 1 to about 30, more preferably 10 to 25.

Another nonionic emulsifying agent(s) that has been found to be suitable in the process of this invention is polyethoxylated alcohol(s) having the general formula:

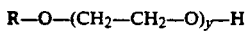

wherein R is an alkyl having from about 7 to about 20 carbon atoms and y is an integer that represents the average number of ethylene oxide units or segments in the emulsifying agent(s), which is the mean of a normal Gaussian distribution curve and is from about 1 to about 100. More preferably, R is an alkyl having from about 7 to about 18 carbon atoms and y is from about 4 to about 30.

The emulsifying agent(s) used in the practice of the invention must enable formation of the coating 80 and retention of stability at ambient temperatures. Unless broad-based for such functionality, a mixture of two or more emulsifiers is employed, and is particularly preferred. A suitable preferred emulsifying agent(s) employed to produce the coating 80 has been determined to be octylphenoxypolyethoxyethanol nonionic surfactant having an average of 33.4 carbon atoms, an average of 60.8 hydrogen atoms, and an average of 10.7 oxygen atoms, and sold commercially under the trademark TRITON® X-100 registered to the Rohm and Haas Co.

The (flexibilizer) agent which furnishes flexibility to the coating 80 may be any agent or composition of matter which provides the coating 80 with flexibility needed in the event the walls of the device 10 are bent or are otherwise deformed and which insures that the coating 80 does not crack and/or crumble off of the inside surface of the walls of the device 10. Preferably the (flexibilizer) agent is a polyhydric alcohol selected from the group consisting of dihydric alcohols, trihydric alcohols, and mixtures thereof. The dihydric alcohols preferably have from 2 to about 8 carbon atoms, and the trihydric alcohols preferably have from 3 to about 8 carbon atoms. Suitable dihydric alcohols have been determined to be ethylene glycol (i.e., glycol), 1,2-propylene glycol, and 1,3-butylene glycol (as well as 1,4-butylene glycol and 2,3-butylene glycol). Suitable trihydric alcohols have been determined to be glycerol (i.e., 1,2,3-propanetriol), 1,2,4-butanetriol, and 1,2,6-hexanetriol. More preferably, the (flexibilizer) agent furnishing flexibility to the coating 80 is glycerol.

The inside surface (e.g. inside surface 23 and/or inside surface 66) of the wall (e.g. wall 20 and/or wall 62) of the device 10 of the present invention may be treated to provide the coating 80 by initially preparing a coating composition and subsequently applying the coating compositions to the inside surface. The coating composition is applied to the inside surface by contacting the inside surface with the coating composition through or by any suitable means, such as, by way of example only, spraying or painting, or brushing or wiping the coating composition onto the inside surface (i.e., inside surface 23 and/or inside surface 66) of the wall (i.e., wall 20 and/or wall 62) of the device 10. The inside surface should be contacted with the coating composition for a sufficient period of time, preferably from about one (1) second to about fifteen (15) minutes in order that the coating composition can dry into the coating 80 as a clear/transparent layer or film which is adhered to the base material from which the wall is manufactured, such as transparent plasticized polyvinyl chloride. When the coating composition dries, the coating 80 is formed having an average thickness of from about one (1) micron to about 75 microns.

The coating composition is prepared by mixing and/or agitating together under ambient conditions a major proportion of a solvent (or carrier fluid), and a minor proportion of the binding agent, the emulsifying agent and the (flexibilizer) agent. As the coating composition dries, the solvent evaporates, leaving adhered to the inside surface of the wall of the device 10 the coating 80 which may also include a residual (preferably miniscule) quantity of solvent that did not evaporate. Mixing and/or agitation may be by any form or means of agitation such as a dynamic shearer or mixer.

The solvent may be any fluid that is capable of forming a compatible solution with the binding agent, the emulsifying agent and the (flexibilizer) agent, and capable of evaporating from the coating composition to cause the formation of the coating 80 bonded to the inside surface as a clear/transparent film or layer. Preferably, the solvent is an alcohol having from one (1) to eight (8) carbon atoms and/or water (i.e., an aqueous medium), and mixtures thereof. More preferably the solvent is ethanol.

The coating composition when prepared preferably comprises a major proportion of the solvent and a minor proportion of the binding agent and the emulsifying agent. The coating composition also preferably comprises a minor proportion of the (flexibilizer) agent. The coating composition when prepared more specifically preferably comprises from about 65% to about 99.4% by weight of the solvent; from about 0.4% to about 40% by weight of the binding agent; from about 0.1% to about 10% by weight of the emulsifying agent; and from about 0.1% to about 15% by weight of the (flexibilizer) agent. More preferably, the coating composition comprises from about 75% by weight to about 98% by weight of the solvent; from about 1% by weight to about 20% by weight of the binding agent; from about 0.2% to about 9% by weight of the emulsifying agent; and from about 0.2% to about 10% by weight of the (flexibilizer) agent. Most preferably, the coating composition comprises from about 92% to about 96% by weight of the solvent; from about 3% to about 7% by weight of the binding agent; from about 0.3% to about 2% by weight of the emulsifying agent; and from about 0.5% to about 4% by weight of the (flexiblizer) agent. In a preferred embodiment of the invention, a preferred coating composition is prepared by initially measuring 95 parts by weight of ethanol into a container and thereafter begin mixing and slowly adding 0.75 parts by weight of glycerin and 0.50 parts by weight of octylphenoxypolyethoxyethanol nonionic surfactant sold commercially under the trademark TRITON® X-100. The resulting solution is continued to be mixed and agitated, and subsequently 2.5 parts by weight of PVP K-30 and 2.5 parts by weight of PVP K-90 are added and the resulting mixture is mixed and agitated until all components are dissolved to form a preferred coating composition. Mixing and agitation periods are for a sufficient period of time to cause the respective components to essentially dissolve in solution and obliterate possible lumping of any components. When the preferred coating composition is liberally sprayed on the inside surface (i.e., inside surface 23 and/or inside surface 66) of the wall (i.e., wall 20 and/or wall 62) of the device 10 a preferred coating 80 results in one (1) to five (5) minutes which is generally the time of evaporation for the ethanol. Typically, the preferred coating 80 would have a thickness of from about 10 microns to about 14 microns, depending on how liberally the coating composition was sprayed.

With continuing reference to the drawings for operation of the device 10, which is believed to be apparent, the catheter 14 is inserted in the usual manner, typically with a needle (not shown) slidably passing through the catheter head 17 and the catheter 14 such that the needle and catheter 14 are generally concentric and the needle forms the piercing instrument when both are inserted into a vein or artery of the body portion 18. Subsequently, the needle is withdrawn, leaving the catheter 14 embedded in the vein or artery. The anchor member 16 is mounted or secured to the body portion 18. The heparin lock 12 is connected to the catheter head 17 after withdrawal of the needle and when there is no desire for a supply hose to be connected to the catheter head 17 for feeding infusion liquid through the catheter 14 and into the vein or artery of a patient. Obviously, the heparin lock 12 may be removed for securing the catheter head 17 to a supply hose that is coupled with a source or supply of infusion liquid (e.g. blood, plasma, glucose water, salt water, and the like). When the heparin lock 12 is secured to the catheter head 17 and it is desirable to protect the catheter 14-catheter head 17 and to protect the body portion 18 from infection and/or moisture, or the like, the device 10 is postured over the catheter head 17-heparin lock 12 while the catheter 14 remains inserted, and the heparin lock 12 is passed slidably into the aperture 28 to hold the catheter head 17 and heparin lock 12 rigidly. The heparin lock 12 seals off the opening defined by the aperture 28. The coating 80 on the inside surface of the wall of the device 10 prevents fogging of a transparent wall. The opening 84 which is covered with the sheet member 86 permits ventilation of the device 10 while keeping fluids from passing into the insides of the device 10.

The device 10 is held against the body portion 18 and in covering relation to the catheter head 17-heparin lock 12 by the flanges (or flanges and ears) being connected or secured to the body portion 18. This mounting, as was previously indicated, may be accomplished by tape (not shown) or adhesive means on the bottom of the flanges or flanges and ears. After the device 10 has been mounted and secured to the body portion 18 in the foregoing cover relation to the catheter head 17-heparin lock 12, a patient may feel free to bath, shower, walk, or perform any other activities with reduced fear of water or moisture contacting the covered body portion 18 and with reduced fear of the catheter head 17-heparin lock 12 being jarred or bumped which could result in serious injury to the vein or artery of the patient from the catheter 14 being abruptly moved therein or completely dislodged therefrom. The continuous face 22, with the aperture 28 being sealed off by the heparin lock 12, more particularly protects the body portion 18, in combination with the remaining solid continuous structure of the device 10.

In view of the foregoing, it is readily apparent that the structure of the present invention has provided an improved device 10 for covering or shielding any needle or catheter-heparin lock combination to preclude inadvertent dislocation of the catheter-heparin lock after initial placement and to assist the body portion 18 from becoming infective due to moisture, germs, etc. The improved device 10 also readily absorbs shock forces thereagainst.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

We claim:

1. A shielding device for protecting an infusion needle comprising a cover having a transparent wall; and a coating means disposed on said transparent wall for maintaining the transparency of said transparent wall, said coating means comprises a major proportion of a binding agent, a minor proportion of an emulsifying agent, and a minor proportion of an agent which causes the coating means to become more flexible.

2. The device of claim 1 wherein said coating means comprises from about 50% to about 99% by weight of the binding agent, from about 0.5% to about 30% by weight of the emulsifying agent; and from about 0.5% to about 30% by weight of said agent which causes the coating means to become more flexible.

3. The device of claim 2 wherein said binding agent comprises a first polyvinylpyrrolidone polymer having an average molecular weight of about 40,000 and a second polyvinylpyrrolidone polymer having an average molecular weight of about 360,000, wherein said first and said second polyvinylpyrrolidone polymer are combined in a weight ratio of about 1:1.

4. A shielding device for holding and protecting an infusion needle comprising a cover having a transparent wall; said transparent wall having an aperture for receiving and holding an infusion needle; and a coating means disposed on said transparent wall for maintaining the transparency of said transparent wall, said coating means comprises a major proportion of a binding agent, a minor proportion of an emulsifying agent, and a minor proportion of an agent which causes the coating means to become more flexible.

5. The shielding device of claim 4 wherein said transparent wall comprises at least one opening; and at least one air permeable sheet means, secured to said wall and covering said opening, for preventing fluids from passing through said opening.

6. The shielding device of claim 5 wherein said air permeable sheet means for preventing fluids from passing comprises spunbonded olefin.

7. The shielding device of claim 6 wherein said spunbonded olefin has a Frazier porosity in ft.$^3$/ft.$^2$/min. selected from the group consisting of 45, 40 and less than 1.

8. The shielding device of claim 4 wherein said coating means comprises from about 50% to about 99% by weight of said binding agent, from about 0.5% to about 30% by weight of said emulsifying agent; and from about 0.5% to about 30% by weight of said agent which causes the coating means to become more flexible.

9. The shielding device of claim 8 wherein said binding agent comprises a first polyvinylpyrrolidone polymer having an average molecular weight of about 40,000 and a second polyvinylpyrrolidone polymer having an average molecular weight of about 360,000, wherein said first and said second polyvinylpyrrolidone polymer are combined in a weight ratio of about 1:1.

10. A device for holding a heparin lock secured to a catheter that is disposed through a body portion at a body entry point and into an artery of a patient, which comprises a hollow generally elongated cover having a transparent wall constructed of generally flexible material and terminating in a generally continuous periphery that forms an opening for being supported on an external surface of said body portion, said wall comprising a face having generally a pair of side edges, a top edge and a bottom edge and an aperture off-set from the side comprising a generally oval-shaped body integrally secured to the face at the pair of side edges and the top edge and tapering rearwardly and downwardly therefrom to terminate in a pair of opposed, generally parallel body edges; and a coating means transparency of said transparent wall; and said coating means comprises a major proportion of a binding agent; a minor proportion of an emulsifying agent; and a minor proportion of an agent which causes the coating means to become more flexible.

11. The device of claim 10 wherein said coating means comprises from about 50% to about 99% by weight of the binding agent, from about 0.5% to about 30% by weight of the emulsifying agent; and from about 0.5% to about 30% by weight of said agent which causes the coating composition to become more flexible.

12. The device of claim 11 wherein said binding agent comprises a first polyvinylpyrrolidone polymer having an average molecular weight of about 40,000 and a second polyvinylpyrrolidone polymer having an average molecular weight of about 360,000, wherein said first and said second polyvinylpyrrolidone polymer are combined in a weight ratio of about 1:1.

13. The device of 10 wherein said coating means has an average thickness of from about 1 micron to about 75 microns.

14. The device of claim 10 wherein said transparent wall comprises at least one opening; and at least one air permeable sheet means, secured to said wall and covering said opening, for preventing fluids from passing through said opening.

15. The device of claim 14 wherein said air permeable sheet means for preventing fluids from passing comprises spunbonded olefin.

16. The device of claim 15 wherein said spunbonded olefin has a Frazier porosity in ft.$^3$/ft.$^2$/min. selected from the group consisting of 45, 40 and less than 1.

* * * * *